United States Patent [19]
Kang et al.

[11] Patent Number: 5,750,724
[45] Date of Patent: May 12, 1998

[54] INDOLEALKYL DERIVATIVES OF BENZODIOXANMETHYLAMINE

[75] Inventors: Young H. Kang, Robbinsville, N.J.; Gary P. Stack, Ambler, Pa.

[73] Assignee: American Home Products Corporation, Madison, N.J.

[21] Appl. No.: 739,912

[22] Filed: Oct. 30, 1996

Related U.S. Application Data

[60] Provisional application No. 60/007,284, Nov. 6, 1995.

[51] Int. Cl.$^6$ .................................................. C07D 405/00
[52] U.S. Cl. .................................................. 548/454
[58] Field of Search .................................................. 548/454

[56] References Cited

U.S. PATENT DOCUMENTS

| | | |
|---|---|---|
| 3,324,143 | 6/1967 | Moed et al. |
| 3,444,210 | 5/1969 | Moed et al. |
| 4,711,893 | 12/1987 | Hausberg et al. |

FOREIGN PATENT DOCUMENTS

| | | |
|---|---|---|
| 464558 | 1/1992 | European Pat. Off. |
| 219114 | 12/1983 | Japan. |

OTHER PUBLICATIONS

Cornfield et al., "MDL 73005EF: partial agonist at the 5-HT$_{1A}$ receptor negatively linked to adenylate cyclase", European Journal of Pharm., 173 (1989) 189–192.

*Primary Examiner*—Deborah Lambkin
*Attorney, Agent, or Firm*—Rebecca R. Barrett

[57] ABSTRACT

The compounds of formula I:

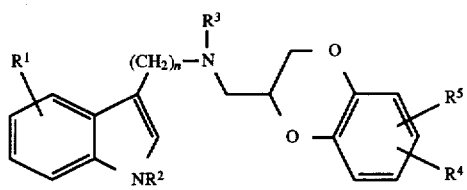

wherein $R^1$, $R^4$ and $R^5$ are, independently, hydrogen, alkyl, alkoxy, aralkoxy, alkanoyloxy, hydroxy, halo, trifluoromethyl, amino, mono- or di-alkylamino, alkanamido, or alkanesulfonamido; or, $R^1$ is defined as above and $R^4$ and $R^5$, taken together, are ortho substituted methylenedioxy, ethylenedioxy, or propylenedioxy; $R^2$ and $R^3$ are, independently, hydrogen or alkyl; n is 3 or 4; or pharmaceutically acceptable salts thereof, are useful in the treatment of depression and related disorders.

27 Claims, No Drawings

INDOLEALKYL DERIVATIVES OF BENZODIOXANMETHYLAMINE

This application claims the benefit of U.S. Provisional Application No. 60/007,284, filed Nov. 6, 1995.

BACKGROUND OF THE INVENTION

Belgian Patent 635,203 discloses compounds of the following formula, in which $R^1$ is H or methyl, $R^2$ is H or OH, n is 0 or 1 and Y is mono- or di-hydroxy, methoxy or methylenedioxy as CNS depressants, tranquilizers and sedatives of long duration and low neurotoxicity.

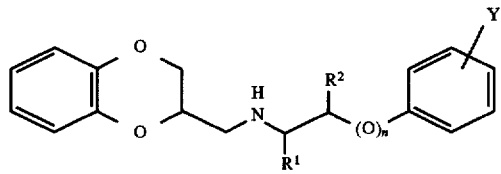

Jpn. Kokai Tokyo Koho 58,219,114 discloses compounds of the following formula, in which X is $OCH_2$, $COCH_2$, NHCO, $S(O)_pCH_2$ (p is 0, 1 or 2), $NRCH_2$ (R is H, alkyl, alkanoyl), $CH_2$, $CH(OH)CH_2$, $OCH_2CH(OH)$ and n and m are 1, 2 or 3, as antihypertensives.

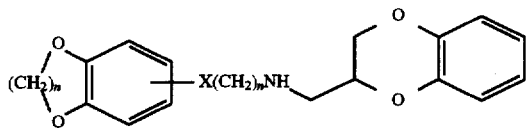

U.S. Pat. No. 4,711,893 discloses hydroxyindole derivatives of the following formula, wherein Ind denotes a 4-, 5-, 6- or 7-hydroxyindole-3-yl radical which can additionally be substituted in the 2 position by alkyl with 1 to 3 carbon atoms and/or substituted in the benzene ring by alkyl with 1 to 3 carbon atoms, F, Cl, Br and/or CN, as agents for lowering blood pressure.

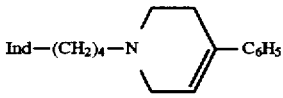

European Patent Application number 91110376.0 describes a series of indolealkyl derivatives of alkoxypyrimidines of the following formula, useful for the treatment of migraine. In the formula, $R^1$ is hydrogen, halogen, or $CH_3SO_2N(R^5)$—, $R^2$, $R^3$ and $R^5$ are independently selected from hydrogen and lower alkyl and $R^4$ is lower alkyl.

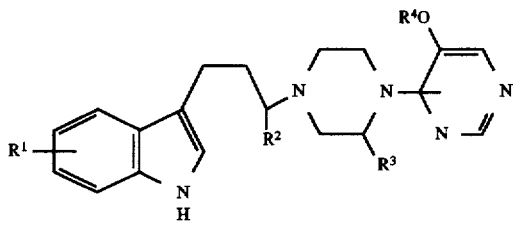

European Journal of Pharmacology, 173 (1989), 189 describes the indoleethylamine of the following formula as having partial agonist activity at 5-$HT_{1A}$ receptors.

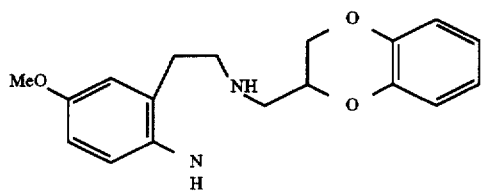

DESCRIPTION OF THE INVENTION

In accordance with this invention, there is provided a group of novel indolepropyl and indolebutyl derivatives of benzodioxanmethylamine useful as antidepressant and antipsychotic agents of formula I:

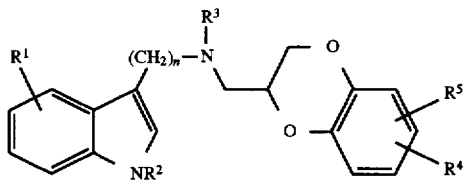

wherein
$R^1$, $R^4$ and $R^5$ are, independently, hydrogen, alkyl of 1–6 carbon atoms, alkoxy of 1–6 carbon atoms, aralkoxy of 7 to 12 carbon atoms, alkanoyloxy of 2 to 6 carbon atoms, hydroxy, halo, trifluoromethyl, amino, mono- or di-alkylamino in which each alkyl group has 1 to 6 carbon atoms, alkanamido of 2 to 6 carbon atoms, or alkanesulfonamido of 1 to 6 carbon atoms; or, $R^1$ is defined as above and $R^4$ and $R^5$, taken together, are ortho substituted methylenedioxy, ethylenedioxy, or propylenedioxy;

$R^2$ and $R^3$ are, independently, hydrogen or alkyl of 1 to 6 carbon atoms;

n is 3 or 4;

or a pharmaceutically acceptable salt thereof.

Of these compounds, the preferred members are those in which $R^1$, $R^4$ and $R^5$ are hydrogen, hydroxy, alkoxy of 1 to 6 carbon atoms, halo, or alkanesulfonamido of 1 to 6 carbon atoms, or $R^1$ is hydrogen, hydroxy, alkoxy of 1 to 6 carbon atoms, halo, or alkanesulfonamido of 1 to 6 carbon atoms and $R^4$ and $R^5$, taken together, are methylenedioxy, $R^2$ and $R^3$ are hydrogen and n is defined as above and pharmaceutically acceptable salts thereof.

Most preferred are those members in which $R^1$ is hydrogen, hydroxy, methoxy or fluoro, $R^2$, $R^3$ and $R^5$ are hydrogen, $R^4$ is hydrogen, hydroxy, methoxy, ethoxy, halo or alkanesulfonamido of 1 to 3 carbon atoms and n is defined as above and pharmaceutically acceptable salts thereof.

This invention relates to both the R and S stereoisomers of the benzodioxan methanamine, as well as to mixtures of the R and S stereoisomers. Throughout this application, the name of the product of this invention, where the absolute configuration of the benzodioxan methanamine is not indicated, is intended to embrace both R and S enantiomers as well as mixtures of the two.

The pharmaceutically acceptable salts are those derived from such organic and inorganic acids as: acetic, lactic, citric, tartaric, succinic, fumaric, maleic, malonic, mandelic, mallic, hydrochloric, hydrobromic, phosphoric, nitric, sulfuric, methanesulfonic, toluenesulfonic and similarly known acceptable acids.

The compounds of this invention are prepared by conventional methods. For example, the appropriately substituted benzodioxan methanamine is combined with a suitable indolealkyl halide or tosylate in the presence of an acid scavenger such as diisopropylethylamine in a solvent such as dimethylformamide and heated at 80°–100° C. for 24 hours (1). Alternatively, a benzodioxan methylhalide or tosylate may be combined with the appropriate indolealkyl amine under similar conditions and heated for an extended period (2). The amine component may also be combined with a suitably substituted, activated carboxylic acid followed by reduction by an agent such as borane/THF or lithium aluminum hydride (3). Preferred methods of activating the indolealkanoic acids and benzodioxan carboxylic acids of the invention include reaction with hydroxybenzotriazole (HOBT) in the presence of diisopropylcarbodiimide (DIC) or conversion to an acid chloride with thionyl chloride in dichloromethane.

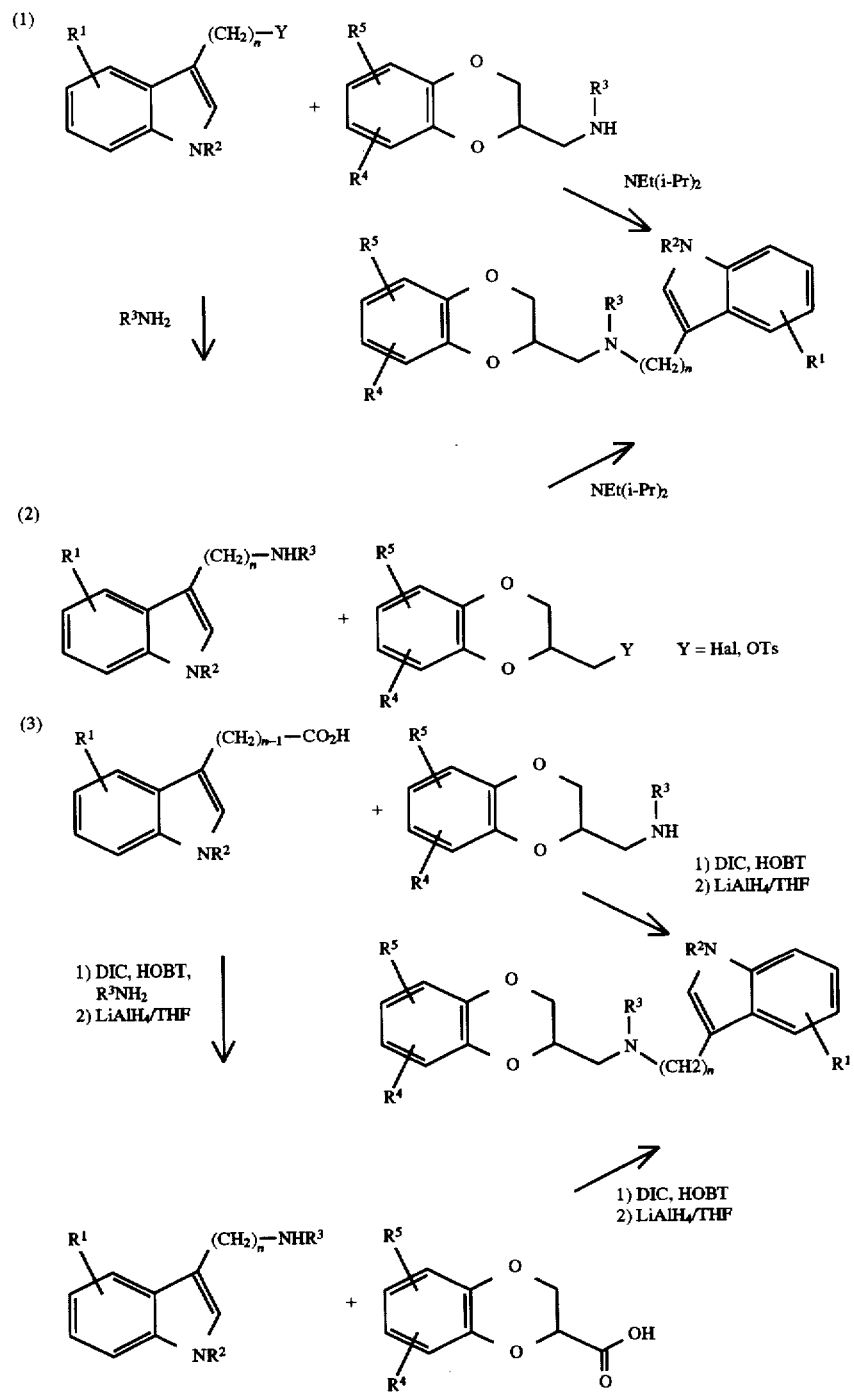

The indolealkyl halides and tosylates appropriate for the above procedures are known compounds; the indolealkylamines may be readily prepared from them as shown above. The indolealkanoic acids and benzodioxan carboxylic acids appropriate to (3) are known compounds or may be readily prepared by one schooled in the art. The benzodioxan methanamines and methylhalides themselves are known compounds, or they can readily be derived from the appropriate salicylaldehyde by the procedure illustrated below. The benzodioxan methanamines may be resolved into their enantiomers by conventional methods or, preferably, they may be prepared directly by substitution of (2R)-(−)-glycidyl 3-nitrobenzenesulfonate or tosylate (for the S benzodioxan methanamine) or (2S)-(+)-glycidyl 3-nitrobenzenesulfonate or tosylate (for the R enantiomer) in place of epichlorohydrin in the procedure below.

203: 105–109, 1991, wherein homogenized rat striatal brain tissue is incubated with $^3$H-quinpirole and various concentrations of test compound, filtered and washed and counted in a Betaplate scintillation counter. The results of this testing with compounds representative of this invention are also given below.

Inhibition of $^3$H 5-hydroxytryptamine uptake was established using a modification of the procedure of Wood and Willie, J. Neurochem. 37:795, 1981. Crude synaptosomes prepared from rat frontal cortex were utilized and nonspecific uptake was defined as that occurring in the presence of excess (10 μM) fluoxetine. $IC_{50}$'s thus determined for stan-

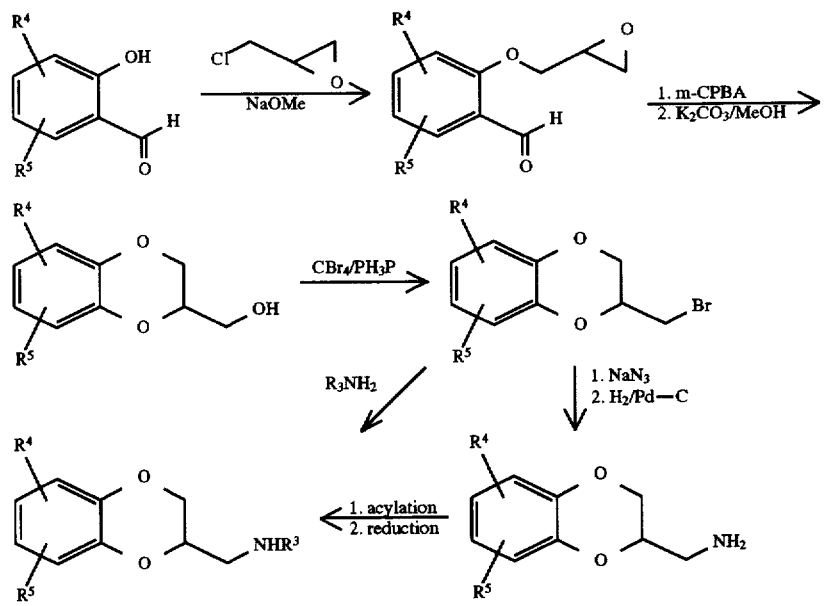

The compounds of this invention possess an unusual profile which combines potent affinity for serotonin 5-HT$_{1A}$ receptors with the ability to inhibit reuptake of serotonin and thus are exceedingly useful for the treatment of depression. Certain of the compounds of the invention also possess high affinity for dopamine D$_2$ receptors and are thus useful for the treatment of psychoses and psychotic depression. Because these ligands interact with serotonin 5-HT$_{1A}$ receptors, they are also useful for the treatment of various CNS disorders such as anxiety, eating disorders, sexual dysfunction, addictive disorders caused by ethanol or cocaine abuse and related illnesses.

High affinity for the serotonin 5-HT$_{1A}$ receptor was established by testing the claimed compound's ability to displace [$^3$H] 8-OHDPAT (dipropylaminotetralin) from the $^5$-HT$_{1A}$ serotonin receptor following the procedure of Hall et al., J. Neurochem. 44, 1685 (1985). This procedure is employed to analogize this property of the claimed compounds with those of buspirone, gepirone and ipsapirone, agents which have demonstrated both anxiolytic and antidepressant activity in clinical trials and which display potent affinity for the 5-H$_{1A}$ serotonin receptor subtype. The anxiolytic and antidepressant activity of these agents are believed to be, at least partially, due to their 5-HT$_{1A}$ receptor affinity (Vander Maclen et al., Eur. J. Pharmacol. 1986, 129 (1–2) 133–130 and Lucki, J. Clin. Psychiat. 1992, 52, 24–31).

Affinity for the dopamine D$_2$ receptor was established by a modification of the standard experimental test procedure of Seemen and Schaus, European Journal of Pharmacology dard clinical antidepressants are 71 nM for fluoxetine, 120 nM for imipramine and 240 nM for zimelidine.

The results of the three standard experimental test procedures described in the preceding three paragraphs were as follows:

| Compound | D$_2$ Receptor Affinity $IC_{50}$ (nM) | 5-HT$_{1A}$ Receptor Affinity $IC_{50}$ (nM) | Inhibition 5-HT Uptake $IC_{50}$ (nM) |
|---|---|---|---|
| Example 1 | 116.00 | 5.60 | |
| Example 2 | 82.00 | 5.70 | |
| Example 3 | 1.30 | 6.00 | |
| Example 4 | 102.00 | 8.05 | |
| Example 5 | 6.50 | 0.06 | 52 |
| Example 6 | 45.00 | 2.70 | |
| Example 7 | 1225.00 | 6.74 | |
| Example 8 | 0.61 | 0.35 | |
| Example 9 | 64.00 | 0.80 | 738 |
| Example 10 | 0.39 | 1.94 | |
| Example 11 | 2.37 | 3.89 | 13.5 |
| Example 12 | 1.55 | 0.10 | 2380 |
| Example 13 | 8.13 | 0.12 | 154 |
| Example 14 | 4.75 | 0.81 | |
| Example 15 | 0.30 | 4.85 | |
| Example 16 | 13.59 | 4.86 | |
| Example 17 | 3.50 | 3.77 | |
| Example 18 | 18.45 | 3.95 | |
| Example 19 | 72.00 | 5.50 | |
| Example 20 | 0.13 | 5.90 | |
| Example 21 | 0.76 | 5.80 | |
| Example 22 | 49.75 | 16.00 | |

-continued

| Compound | D$_2$ Receptor Affinity IC$_{50}$ (nM) | 5-HT$_{1A}$ Receptor Affinity IC$_{50}$ (nM) | Inhibition 5-HT Uptake IC$_{50}$ (nM) |
|---|---|---|---|
| Example 23 | 6.63 | 0.56 | |
| Example 24 | 20.45 | 9.29 | |

Hence, the compounds of this invention demonstrated high affinity for the serotonin 5-HT$_{1A}$ receptor subtype, as well as the ability to block the reuptake of serotonin and are therefore useful in the treatment of depression and related CNS disorders such as anxiety, sexual dysfunction, eating disorders, addictive disorders caused by ethanol or cocaine abuse and related illnesses. Certain of the members of the invention also demonstrated high affinity for dopamine D$_2$ receptors and are thus useful in the treatment of schizophrenia and psychotic depression.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintergrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific state of depression or psychosis must be subjectively determined by the attending physician. The variables involved include the specific state of depression or psychosis and the size, age and response pattern of the patient. As with all antidepressant/antipsychotic agents, the most desirable dosage regimen for a given patient is determined by beginning treatment at a low dose and then increasing the dose to achieve the desired effect.

Based upon the potency of buspirone at the 5HT$_A$ receptor at about an IC$_{50}$ of 30 nM and a daily human dose range from about 15 to about 65 mg/day, the compounds of this invention would be dosed initially at about 0.05 mg/day and increased gradually to a maximum dosage of about 50 mg/day for the least potent compound indicated, supra.

The following examples illustrate the production of representative compounds of this invention.

EXAMPLE 1

[(6,7-Dihydro-1,3-dioxolo[4,5-g][1,4]benzodioxin-6-yl)methyl]-[4-(1H-indol-3-yl)-butyl]-amine To 2.0 g (10 mmole) of indolebutyric acid in 100 ml of dimethylformamide (DMF) was added 1.5 g (10 mmole) of hydroxybenzotriazole hydrate and 1.3 g (10 mmole) of diisopropyl carbodiimide. The mixture was stirred at room temperature for two hours. (S)-6,7-methylenedioxybenzodioxan-2-methanamine (2.1 g, 10 mmole) was then added and stirring continued at room temperature for 15 hours. The solvent was removed in vacuum and replaced with 250 ml of methylene chloride. The mixture was washed with 150 ml portions of 2N HCl, saturated sodium bicarbonate solution and brine and dried over sodium sulfate. Filtration, concentration in vacuum and column chromatography on 100 g of silica gel with methylene chloride as the eluant gave 3.0 g of the desired amide.

Lithium aluminum hydride (0.86 g, 22.8 mmole) in dry tetrahydrofuran (THF) (100 ml) was placed in a three-neck flask which was flushed with nitrogen. The amide (3.0 g, 7.6 mmole) prepared above in 50 ml of dry THF was slowly introduced through a syringe to the LAH suspension in an ice-bath. The mixture was then stirred at gentle reflux for 48 hours. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was then dried over anhydrous sodium sulfate, filtered and concentrated to give the free base of the desired product as an oily white solid (1.4 g, 3.7 mmole, 48%). The free base of the product was dissolved in ethanol-diethyl ether (1:1) and treated with 4N isopropanolic HCl (0.9 ml, 3.6 mmole) to give the (S) enantiomer of the title compound as a white solid, hydrochloride salt, m.p. 185°–186° C.

Elemental Analysis for: C$_{22}$H$_{24}$N$_2$O$_4$.HCl Calc'd: C, 63.38; H, 6.04; N, 6.72 Found: C, 63.42; H, 6.09; N, 6.63

EXAMPLE 2

[4-(1H-Indol-3-yl)-butyl]-(7-methoxy-2,3-dihydro-benzo[1,4]dioxin-2-ylmethyl)amine 3-Indolebutyric acid (1.3 g, 6.5 mmole), 1-hydroxybenzotriazole hydrate (1.1 g, 7.8 mmole) and 1,3-diisopropylcarbodiimide (2.4 ml, 15.6 mmole) were combined in 100 ml of DMF and stirred at room temperature for 2 hours under a nitrogen atmosphere. To this was added dropwise (S)-7-methoxy-2,3-dihydro-1,4-benzodioxin-2-methanamine hydrochloride (1.5 g, 6.5 mmole) in 50 ml of DMF and the mixture was further stirred for 24 hours. The solvent was removed and replaced with dichloromethane. The mixture was then washed with $H_2O$. The separated organic layer was dried over anhydrous sodium sulfate, filtered and concentrated in vacuum. The residue was chromatographed on a silica gel column using ethyl acetate as the eluant. Evaporation of product fractions gave 1.5 g (61%) of the desired product, (S)-(7-methoxy-2,3-dihydro-benzo[1,4]dioxin-2-ylmethyl)-4-(1H-indol-3-yl)-butanamide, as a foam.

Lithium aluminum hydride (0.74 g, 19.5 mmole) in dry THF (100 ml) was placed in a three-neck flask which was flushed with nitrogen. The amide (1.5 g, 3.9 mmole) prepared above in 50 ml of dry THF was slowly introduced through a syringe to the LAH suspension in an ice-bath. The mixture was then stirred at gentle reflux for 48 hours. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was then dried over anhydrous sodium sulfate, filtered and concentrated. The crude product was chromatographed on a silica gel using first ethyl acetate/ hexane (9/1) and then ethyl acetate as eluants to give 0.8 g (56%, 2.2 mmole) of the free base of expected product as an oil. The free base was dissolved in ethanol, treated with 4N isopropanolic HCl (1.1 ml, 4.4 mmole) and precipitated with diethyl ether to give the (S) enantiomer of the title compound as a white solid, mono-hydrochloride salt, m.p. 157°–158° C.

Elemental Analysis for: $C_{22}H_{26}N_2O_3 \cdot HCl$ Calc'd: C, 65.58; H, 6.75; N, 6.95 Found: C, 65.28; H, 6.65; N, 6.75

EXAMPLE 3

3-{[4-(1H-Indol-3-yl)-butylamino]-methyl}-2,3-dihydro-benzo[1,4]dioxin-6-ol

3-Indolebutyric acid (1.0 g, 5.0 mmole), 1-hydroxybenzotriazole hydrate (0.8 g, 6.0 mmole) and 1,3-diisopropylcarbodiimide (1.9 ml, 12.0 mmole) were combined in 100 ml of DMF and stirred at room temperature for 2 hours under a nitrogen atmosphere. To this was added dropwise 7-hydroxy-2,3-dihydro-1,4-benzodioxin-2-methanamine hydrochloride (1.1 g, 5.0 mmole) in 50 ml of DMF and the mixture was further stirred for 24 hours. The solvent was removed and replaced with dichloromethane. The mixture was then washed with $H_2O$. The separated organic layer was dried over anhydrous sodium sulfate, filtered and concentrated in vacuum. Chromatography on silica gel using first dichloromethane and then 2.5% methanol in dichloromethane as eluants gave 0.3 g (16%) of the desired product, (7-hydroxy-2,3-dihydro-benzo[1,4]dioxin-2-methyl)-4-(1H-indol-3-yl)-butanamide, as an oil.

Lithium aluminum hydride (0.30 g, 8.0 mmole) in dry THF (50 ml) was placed in a three-neck flask which was flushed with nitrogen. The amide (0.3 g, 0.8 mmole) prepared above in 20 ml of dry THF was slowly introduced through a syringe to the LAH suspension in an ice-bath. The mixture was then stirred at gentle reflux for 24 hours. After the reaction mixture was cooled to room temperature, the hydride was carefully destroyed with 3 ml of 1:1 mixture of THF and water in an ice-bath. Stirring was continued as 10 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using first 2.5% and then 5% methanol in dichloromethane as eluants to give 0.1 g (38%, 0.3 mmole) of the free base of expected product. The free base was dissolved in methanol, treated with 4N isopropanolic HCl (0.14 ml, 0.56 mmole) and precipitated with diethyl ether to give the title compound as a white solid, hydrochloride, quarter hydrate, m.p. 205°–207° C.

Elemental Analysis for: $C_{21}H_{24}N_2O_3 \cdot HCl \cdot \frac{1}{4} H_2O$ Calc'd: C, 64.11; H, 6.53; N, 7.12 Found: C, 64.38; H, 6.52; N, 7.12

EXAMPLE 4

[3-(5-Benzyloxy-1H-indol-3-yl)-propyl]-(2,3-dihydro-benzo[1,4]dioxin-2-ylmethyl)-amine 5-Benzyloxyindole-3-propionic acid (2.7 g, 9.1 mmole), 1-hydroxybenzotriazole hydrate (1.5 g, 10.9 mmole) and 1,3-diisopropylcarbodiimide (3.4 ml, 21.8 mmole) were combined in 200 ml of DMF and stirred at room temperature for 2 hours under a nitrogen atmosphere. To this was added dropwise 2,3-dihydro-1,4-benzodioxin-2-methanamine hydrochloride (1.8 g, 9.1 mmole) in 50 ml of DMF and the mixture was further stirred for 24 hours. The solvent was removed and replaced with dichloromethane. The mixture was then washed with $H_2O$. The separated organic layer was dried over anhydrous sodium sulfate, filtered and concentrated in vacuum. The residue was chromatographed on silica gel using first dichloromethane and then 2.5% methanol in dichloromethane as eluants to give 3.2 g (79%) of the desired product, (2,3-dihydro-benzo[1,4]dioxin-2-ylmethyl)-3-(5-benzyloxy-1H-indol-3-yl)-propanamide, as a light tan solid.

Lithium aluminum hydride (2.7 g, 72 mmole) in dry THF (200 ml) was placed in a three-neck flask which was flushed with nitrogen. The amide (3.2 g, 7.2 mmole) prepared above in 75 ml of dry THF was slowly introduced through a syringe to the LAH suspension in an ice-bath. The mixture was then stirred at gentle reflux for 24 hours. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with methylene chloride/isopropanol (3/1) solution. The filtrate was dried over anhydrous sodium sulfate, filtered and concentrated. The gummy product (2.7 g), which was pure enough without further purification, was taken up in diethyl ether and dissolved completely by adding a minimum amount of ethanol. The solution was treated with 4N isopropanolic HCl until pH<3 to afford the title compound as an off-white solid, mono-hydrochloride (0.7 g) of m.p. 212°–214° C.

Elemental Analysis for: $C_{27}H_{28}N_2O_3 \cdot HCl$ Calc'd: C, 69.74; H, 6.07; N, 6.03 Found: C, 69.60; H, 6.39; N, 5.92

EXAMPLE 5

3-{3-[(2,3-Dihydro-benzo[1,4]dioxin-2-ylmethyl)-amino]-propyl}-1H-indol-5-ol

The benzyloxy compound (2.0 g, 4.7 mmole) recovered from the mother liquor above in Example 4, was hydrogenated for 24 hours in methanol (200 ml) with 0.5 g of 10% palladium on carbon. The catalyst was filtered off and the filtrate was concentrated to afford a foam. The crude product was chromatographed on a silica gel column using ethyl acetate as the eluant to give the free base (0.83 g, 2.5 mmole, 52%) of the desired product. The free base was treated with 0.25M of fumaric acid in ethanol (11.0 ml, 2.75 mmole) and diluted with 20 ml of ethanol to give the title compound as a light tan solid, (2:1) fumarate, quarter hydrate, m.p. 222°–223° C.

Elemental Analysis for: $C_{20}H_{22}N_2O_3 \cdot \frac{1}{2}C_4H_4O_4 \cdot \frac{1}{4}H_2O$ Calc'd: C, 65.90; H, 6.16; N, 6.99 Found: C, 65.97; H, 6.05; N, 7.05

EXAMPLE 6

3-{3-[(7-Methoxy-2,3-dihydro-benzo[1,4]dioxin-2-ylmethyl)-amino]-propyl}-1H-indol-5-ol 5-Benzyloxyindole-3-propionic acid (1.8 g, 6.0 mmole), 1-hydroxybenzotriazole hydrate (0.97 g, 7.2 mmole) and 1,3-diisopropylcarbodiimide (2.3 ml, 14.4 mmole) were combined in 150 ml of DMF and stirred at room temperature for 2 hours under a nitrogen atmosphere. To this was added dropwise 7-methoxy-2,3-dihydro-1,4-benzodioxin-2-methanamine hydrochloride (1.4 g, 6.0 hydrochloride (1.4 g, 6.0 mmole) in 50 ml of DMF and the mixture was further stirred for 48 hours. The solvent was removed and replaced with dichloromethane. The mixture was then washed with $H_2O$. The separated organic layer was dried over anhydrous sodium sulfate, filtered and concentrated in vacuum. The residue was chromatographed on a silica gel using first dichloromethane and then 2.5% methanol in dichloromethane as eluants to give 2.6 g (90%) of the desired product, (7-methoxy-2,3-dihydrobenzo[1,4]dioxin-2-ylmethyl)-3-(5-benzyloxy-1H-indol-3-yl)-propanamide, as a light tan solid.

Lithium aluminum hydride (2.0 g, 54 mmole) in dry THF (200 ml) was placed in a three-neck flask which was flushed with nitrogen. The amide (2.6 g, 5.4 mmole) prepared above in 75 ml of dry THF was slowly introduced through a syringe to the LAH suspension in an ice-bath. The mixture was then stirred at gentle reflux for 24 hours. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was taken up in diethyl ether and filtered to remove insoluble material. The ether solution was treated with 4N isopropanolic HCl until pH<3 to precipitate a solid, which was recrystallized from ethanol to give a white solid (1.8 g) of [3-(5-benzyloxy-1H-indol-3-yl)-propyl]-(7-methoxy-2,3-dihydro-benzo[1,4]dioxin-2-ylmethyl)-amine hydrochloride, m.p. 212°–214° C.

Elemental Analysis for: $C_{28}H_{30}N_2O_4 \cdot HCl$ Calc'd: C, 67.94; H, 6.31; N, 5.66. Found: C, 68.14; H, 6.24; N, 5.66.

The benzyloxy compound (1.3 g, 2.6 mmole) prepared above was hydrogenated for 24 hours in methanol (150 ml) with 0.3 g of 10% palladium on carbon. The catalyst was filtered off and the filtrate was concentrated in vacuum. The residue was chromatographed on silica gel using first ethyl acetate and then 2.5% methanol in ethyl acetate as eluants to give the free base (0.3 g, 0.8 mmole, 31%) of the desired product. The free base was treated with 0.25M fumaric acid in ethanol (3.6 ml, 0.90 mmole) and diluted with an additional 10 ml of ethanol. A small amount of hexane was added to precipitate the title compound as an off-white solid, (2:1) fumarate, m.p. 159°–160° C.

Elemental Analysis for: $C_{21}H_{24}N_2O_4 \cdot 1/2 C_4H_4O_4$ Calc'd: C, 64.78; H, 6.14; N, 6.57 Found: C, 64.54; H, 6.22; N, 6.55

EXAMPLE 7

(7-Methoxy-2,3-dihydro-benzo[1,4]dioxin-2-ylmethyl)-[3-(5-methoxy-1H-indol-3-yl)-propyl]-methyl-amine 7-Methoxy-2,3-dihydro-1,4-benzodioxin-2-(N-methyl)-methanamine hydrochloride (0.84 g, 7.5 mmole) in DMF (50 ml) was slowly added to the mixture of 5-methoxy-3-(3-bromopropyl)indole (2.0 g, 7.5 mmole) and diisopropylethylamine (6.5 ml, 37 mmole) in 100 ml of DMF with stirring and the mixture was heated at 80° C. for 24 hours. Most of DMF was removed and the residue was partitioned between dichloromethane and saturated aqueous sodium bicarbonate. The organic phase was separated and dried over anhydrous sodium sulfate, filtered and concentrated in vacuum. The residue was chromatographed on silica gel using ethyl acetate as the eluant. The combined fractions of the free base of desired product (0.76 g, 1.9 mmole, 26%) were concentrated, treated with 0.25M fumaric acid in ethanol (8.4 ml, 2.1 mmole), diluted first with 20 ml of isopropanol and then with a minimum amount of hexane to afford the title compound as a light tan solid, (2:1) fumarate, m.p. 133°–134° C.

Elemental Analysis for: $C_{23}H_{28}N_2O_4 \cdot \frac{1}{2}C_4H_4O_4$ Calc'd: C, 66.06; H, 6.65; N, 6.16 Found: C, 65.66; H, 6.58; N, 6.13

EXAMPLE 8

3-{3-[(7-Hydroxy-2,3-dihydro-benzo[1,4]dioxin-2-ylmethyl)-amino]-propyl}-1H-indol-5-ol 5-Benzyloxyindole-3-propionic acid (1.5 g, 5.0 mmole), 1-hydroxybenzotriazole hydrate (0.8 g, 6.0 mmole) and 1,3-diisopropylcarbodiimide (1.9 ml, 12.0 mmole) were combined in 150 ml of DMF and stirred at room temperature for 2 hours under a nitrogen atmosphere. To this was added dropwise 7-hydroxy-2,3-dihydro-1,4-benzodioxin-2-methanamine hydrochloride (1.1 g, 5.0 mmole) in 50 ml of DMF and the mixture was further stirred for 48 hours. The solvent was removed and replaced with dichloromethane. The mixture was then washed with $H_2O$. The separated organic layer was dried over anhydrous sodium sulfate, filtered and concentrated in vacuum. The residue was chromatographed on silica gel using ethyl acetate as eluant. Fractions containing product were concentrated and recrystallized from ethyl acetate to give 1.6 g (68%) of the desired product, (7-hydroxy-2,3-dihydro-benzo[1,4]dioxin-2-ylmethyl)-3-(5-hydroxy-1H-indol-3-yl)-propanamide, as a white solid.

Lithium aluminum hydride (1.3 g, 34 mmole) in dry THF (100 ml) was placed in a three-neck flask which was flushed with nitrogen. The amide (1.6 g, 3.4 mmole) prepared above in 50 ml of dry THF was slowly introduced through a syringe to the LAH suspension in an ice-bath. The mixture was then stirred at gentle reflux and heating was discontinued after 4 hours reflux due to the formation of a sticky deposit on the wall of the flask. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered off and washed with dichloromethane/isopropanol (3/1) solution. The filtrate was dried over anhydrous sodium sulfate, filtered and concentrated. The crude product was chromatographed on silica gel using first 2.5% and then 5% methanol in dichloromethane as eluants to give the free base of the expected product (0.2 g) as a white solid.

The benzyloxy compound (0.2 g, 4.7 mmole) prepared above was hydrogenated for 24 hours in ethanol (100 ml) with 0.02 g of 10% palladium on carbon as catalyst. The catalyst was filtered off and the filtrate was treated with 0.25M of fumaric acid in ethanol (1.9 ml, 0.48 mmole) to give 0.2 g of the title compound as a white solid, (2:1) fumarate, three-quarter hydrate, m.p. 140°–144° C.

Elemental Analysis for: $C_{20}H_{22}N_2O_4 \cdot \frac{1}{2}C_4H_4O_4 \cdot 3/4$ H2O Calc'd: C, 62.03; H, 6.03; N, 6.58 Found: C, 62.28; H, 6.04; N, 6.50

EXAMPLE 9

(7-Methoxy-2,3-dihydro-benzo[1,4]dioxin-2-ylmethyl)-[4-(5-methoxy-1 H-indol-3-yl)-butyl]-amine 5-Methoxyindole-3-butyric acid (1.0 g, 4.3 mmole), 1-hydroxybenzotriazole hydrate (0.7 g, 5.2 mmole) and 1,3-diisopropylcarbodiimide (1.6 ml, 10.3 mmole) were combined in 150 ml of DMF and stirred at room temperature for 2 hours under a nitrogen atmosphere. To this was added dropwise 7-methoxy-2,3-dihydro-1,4-benzodioxin-2-methanamine hydrochloride (1.0 g, 4.3 mmole) in 50 ml of DMF and the mixture was further stirred for 24 hours. The solvent was removed and replaced with dichloromethane. The mixture was then washed with $H_2O$. The separated organic layer was dried over anhydrous sodium sulfate, filtered and concentrated in vacuum. The residue was chromatographed on a silica gel column using ethyl acetate as eluant. Evaporation of product-containing fractions gave 1.3 g (74%) of the desired product, (7-methoxy-2,3-dihydro-benzo[1,4]dioxin-2-ylmethyl)-4-(5-methoxy-1H-indol-3-as an off-white solid.

Lithium aluminum hydride (1.2 g, 32 mmole) in dry THF (150 ml) was placed in a three-neck flask which was flushed with nitrogen. The amide (1.3 g, 3.2 mmole) prepared above in 50 ml of dry THF was slowly introduced through a syringe to the LAH suspension in an ice-bath. The mixture was then stirred at gentle reflux for 24 hours. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using first ethyl acetate and then 2.5% methanol in ethyl acetate as eluants to give 0.55 g (43%, 1.4 mmole) of the free base of the expected product as a colorless oil. The free base was dissolved in ethanol-diethyl ether (1:1) and treated with 0.25M maleic acid in ethanol (6 ml, 0.28 mmole) to give the title compound as a white solid, (1:1) maleate salt, m.p. 133°–134° C.

Elemental Analysis for: $C_{23}H_{28}N_2O_4 \cdot C_4H_4O_4$ Calc'd: C, 63.25; H, 6.29; N, 5.47 Found: C, 63.25; H, 6.21; N, 5.42

EXAMPLE 10

3-{[4-(5-Methoxy-1H-indol-3-yl)-butylamino]methyl}-2,3-dihydrobenzo[1,4]dioxin-6-ol 5-Methoxyindole-3-butyric acid (1.5 g, 6.4 mmole), 1-hydroxybenzotriazole hydrate (1.0 g, 7.7 mmole) and 1,3-diisopropylcarbodiimide (2.4 ml, 15.4 mmole) were combined in 150 ml of DMF and stirred at room temperature for 2 hours under a nitrogen atmosphere. To this was added dropwise 7-hydroxy-2,3-dihydro-1,4-benzodioxin-2-methanamine hydrochloride (1.4 g, 6.4 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using first ethyl acetate and then 5% methanol in ethyl acetate as eluants. Evaporation of product-containing fractions gave 1.6 g (63%) of the desired product, (7-hydroxy-2,3-dihydro-benzo[1,4]dioxin-2-ylmethyl)-4-(5-methoxy-1H-indol-3-yl)-butanamide, as an oily solid.

Lithium aluminum hydride (1.5 g, 40 mmole) in dry THF (150 ml) was placed in a three-necked flask which was flushed with nitrogen. The amide (1.6 g, 4.0 mmole) prepared above in 50 ml of dry TBF was slowly introduced through a syringe to the LAH suspension in an ice-bath. The mixture was then stirred at gentle reflux for 24 hours. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using 2.5% methanol in ethyl acetate to give 0.6 g (39%, 1.6 mmole) of the free base of the expected product as a white solid. The free base was treated with 0.25M fumaric acid in ethanol (7.0 ml, 1.8 mmole), diluted first with 20 ml of isopropanol and then with a minimum amount of hexane to give the title compound as a white solid, (2:1) fumarate, quarter hydrate, m.p. 110°–113° C.

Elemental Analysis for: $C_{22}H_{26}N_2O_4 \cdot \frac{1}{2}C_4H_4O_4 \cdot \frac{1}{4}H_2O$ Calc'd: C, 64.77; H, 6.45; N, 6.30 Found: C, 64.80; H, 6.35; N, 6.16

EXAMPLE 11

N-(3-{[4-(1 H-Indol-3-yl)-butylamino]-methyl}-2,3-dihydro-benzo[1,4]dioxin-6-yl)-methanesulfonamide 3-Indolebutyric acid (1.7 g, 8.2 mmole), 1-hydroxybenzotriazole hydrate (1.3 g, 9.8 mmole) and 1,3-diisopropylcarbodiimide (1.5 ml, 9.8 mmole) were combined in 200 ml of DMF and stirred at room temperature for 2 hours under a nitrogen atmosphere. To this was added dropwise 7-methylsulfonylamino-2,3-dihydro-1,4-benzodioxin-2-methanamine (2.0 g, 8.2 mmole) in 50 ml of DMF and the mixture was further stirred for 48 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Product fractions were concentrated and washed with a minimum amount of THF to remove a by-product and give 3.0 g (82%) of the desired product, (7-methylsulfonylamino-2,3-dihydro-benzo[1,4]dioxin-2-ylmethyl)-4-(1H-indol-3-yl)-butanamide, as an oily white solid.

Lithium aluminum hydride (2.6 g, 68 mmole) in dry THF (200 ml) was placed in a three-neck flask which was flushed with nitrogen. The amide (3.0 g, 6.8 mmole) prepared above in 75 ml of dry THF was slowly introduced through a syringe to the LAH suspension in an ice-bath. The mixture was then stirred at gentle reflux and heating was discontinued after 5 hours due to the formation of a sticky deposit on the wall of the flask. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using 2.5% methanol in ethyl acetate to give 1.2 g (41%, 3.0 mmole) of the free base of the expected product as a white foam. The free base was treated with 0.25M fumaric acid in ethanol (6.6 ml, 1.6 mmole) and diluted with ethanol until it dissolved. To this was added first an equal volume of diethyl ether and then a minimum amount of hexane to precipitate the title compound as a white solid, (2:1) fumarate, quarter hydrate, m.p. 128°–131° C.

Elemental Analysis for: $C_{22}H_{27}N_3O_4S.\frac{1}{2}C_4H_4O_4.\frac{1}{4}H_2O$ Calc'd: C, 58.58; H, 6.04; N, 8.54 Found: C, 58.23; H, 5.94; N, 8.39

EXAMPLE 12

(2,3-Dihydro-benzo[1,4]dioxin-2-ylmethyl)-[3-(5-methoxy-1H-indol-3-yl)-propyl]-amine 2,3-Dihydro-1,4-benzodioxin-2-methanamine hydrochloride (2.3 g, 11.0 mmole) in DMF (100 ml) was slowly added to a mixture of 5-methoxy-3-(3-bromopropyl)indole (3.0 g, 11.0 mmole) and diisopropylethylamine (9.7 ml, 55 mmole) in 100 ml of DMF with stirring and the mixture was heated at 80° C. for 24 hours. Most of DMF was removed in vacuum and the residue was partitioned between dichloromethane and saturated aqueous sodium bicarbonate. The dichloromethane solution was dried over anhydrous sodium sulfate, filtered, concentrated in vacuum and chromatographed on silica gel using ethyl acetate as the eluant. The combined fractions of free base of the expected product (1.3 g, 3.7 mmole, 34%) were concentrated, treated with 0.25M of fumaric acid in ethanol (8.1 ml, 2.0 mmole) and diluted first with 50 ml of ethanol-diethyl ether (1:1) and then with a minimum amount of hexane to precipitate the title compound as a white solid, (2:1) fumarate salt, m.p. 135°–136° C.

Elemental Analysis for: $C_{21}H_{24}N_2O_3.\frac{1}{2}C_4H_4O_4$ Calc'd: C, 67.30; H, 6.38; N, 6.82 Found: C, 66.94; H, 6.31; N, 6.66

EXAMPLE 13

(2,3-Dihydro-benzo[1,4]dioxin-2-ylmethyl)-[3-(5-fluoro-1H-indol-3-yl)-propyl]-amine 2,3-Dihydro-1,4-benzodioxin-2-methanamine hydrochloride (2.0 g, 10.0 mmole) in DMF (100 ml) was slowly added to the mixture of 5-fluoro-3-(3-bromopropyl)indole (2.6 g, 10.0 mmole) and diisopropylethylamine (8.7 ml, 50 mmole) in 100 ml of DMF with stirring and the mixture was heated at 80° C. for 24 hours. Most of DMF was removed and the residue was partitioned between dichloromethane and saturated aqueous sodium bicarbonate. The dichloromethane solution was dried over anhydrous sodium sulfate, filtered, concentrated in vacuum and column chromatographed on silica gel using ethyl acetate as the eluant. The combined fractions of free base of the expected product (0.5 g, 1.6 mmole, 15%) were concentrated, dissolved in 50 ml of ethanol-diethyl ether (1:1). To this was added 0.25M of fumaric acid in ethanol (3.4 ml, 0.85 mmole) and then a minimum amount of hexane to precipitate the title compound as a light tan solid, (2:1) fumarate salt, m.p. 186°–188° C.

Elemental Analysis for: $C_{20}H_{21}FN_2O_2.\frac{1}{2}C_4H_4O_4$ Calc'd: C, 66.32; H, 5.82; N, 7.03 Found: C, 66.02; H, 5.95; N, 6.85

EXAMPLE 14

N-(3-{[4-(5-Methoxy-1 H-indol-3-yl)-butylamino]-methyl}-2,3-dihydrobenzo[1,4]dioxin-6-yl)-methanesulfonamide 5-Methoxyindole-3-butyric acid (0.75 g, 3.2 mmole), 1-hydroxybenzotriazole hydrate (0.52 g, 3.8 mmole) and 1,3-diisopropylcarbodiimide (1.2 ml, 7.6 mmole) were combined in 100 ml of DMF and stirred at room temperature for 2 hours under a nitrogen atmosphere. To this was added dropwise 7-methylsulfonylamino-2,3-dihydro-1,4-benzodioxin-2-methanamine hydrochloride (0.9 g, 3.2 mmole) in 50 ml of DMF and the mixture was further stirred for 48 hours. The solvent was removed and the residue partitioned between dichloromethane and water. The separated dichloromethane layer was dried over anhydrous sodium sulfate, filtered and concentrated in vacuum. The residue was chromatographed on a silica gel column using first ethyl acetate and then 2.5% methanol in ethyl acetate as eluants. Fractions were concentrated and washed with a minimum amount of THF to remove a byproduct and to give 1.2 g (79%) of the desired product, (7-methylsulfonyl amino-2,3-dihydro-benzo[1,4]dioxin-2-ylmethyl)-4-(5-methoxy-1H-indol-3-yl)-butanamide, as a oily white solid.

Lithium aluminum hydride (0.96 g, 25 mmole) in dry THF (100 ml) was placed in a three-neck flask which was flushed with nitrogen. The amide (1.2 g, 2.5 mmole) prepared above in 50 ml of dry THF was slowly introduced through a syringe to the LAH suspension in an ice-bath. The mixture was then stirred at gentle reflux for 24 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using first ethyl acetate and then 2.5% methanol in ethyl acetate to give 0.4 g (35%, 0.9 mmole) of the free base of the expected product as a colorless oil. The free base was dissolved in ethanol, treated with 0.25M fumaric acid in ethanol (1.9 ml, 0.48 mmole) and precipitated with several drops of hexane to give the title compound as an off-white fluffy solid, (2:1) fumarate, hemihydrate, which was stored in a desiccator right after filtration, m.p. 115°–118° C.

Elemental Analysis for: $C_{23}H_{29}N_3O_5S.\frac{1}{2}C_4H_4O_4.\frac{1}{2}H_2O$ Calc'd: C, 57.02; H, 6.13; N, 7.98 Found: C, 57.07; H, 6.09; N, 7.91

EXAMPLE 15

3-{[4-(1H-Indol-3-yl)-propylamino]-methyl}-2,3-dihydro-benzo[1,4]dioxin-6-ol

3-Indolepropionic acid (1.1 g, 6.0 mmole), 1-hydroxybenzotriazole hydrate (0.97 g, 7.2 mmole) and 1,3-diisopropylcarbodiimide (2.3 ml, 14.4 mmole) were combined in 100 ml of DMF and stirred at room temperature for 2 hours under a nitrogen atmosphere. To this was added dropwise 7-hydroxy-2,3-dihydro-1,4-benzodioxin-2-methanamine hydrochloride (1.3 g, 6.0 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions containing product were concentrated and washed with a minimum amount of THF to remove a by-product and to give 1.3 g (61%) of the desired product, (7-hydroxy-2,3-dihydro-benzo[1,4]dioxin-2-ylmethyl)3-(1H-indol-3-yl)-propanamide, as an off-white oily solid.

Lithium aluminum hydride (1.4 g, 37 mmole) in dry THF (100 ml) was placed in a three-neck flask which was flushed with nitrogen. The amide (1.3 g, 3.7 mmole) prepared above in 50 ml of dry THF was slowly introduced through a syringe to the LAH suspension in an ice-bath. The mixture was then stirred at gentle reflux for 24 hours. After the reaction mixture was cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using first ethyl acetate and then 2.5% methanol in ethyl acetate to give 0.65 g (51%, 1.9 mmole) of the free base of the expected product as an oil. The free base was dissolved in 40 ml of ethanol-diethyl ether (1:1), treated with 0.25M fumaric acid in ethanol (4.2 ml, 1.05 mmole) and precipitated with a minimum amount of hexane to give the title compound as a white solid, (2:1) fumarate salt, m.p. 205°–206° C.

Elemental Analysis for: $C_{20}H_{22}N_2O_3 \cdot \frac{1}{2}C_4H_4O_4$ Calc'd: C, 66.65; H, 6.10; N, 7.07 Found: C, 66.55; H, 6.14; N, 6.97

EXAMPLE 16

(2,3-Dihydro-benzo[1,4]dioxin-2-ylmethyl)-[4-(1H-indol-3-yl)-butyl]-amine

3-Indolebutyric acid (1.2 g, 6.0 mmole), 1-hydroxybenzotriazole hydrate (0.97 g, 7.2 mmole) and 1,3-diisopropylcarbodiimide (2.3 ml, 14.4 mmole) were combined in 100 ml of DMF and stirred at room temperature for 2 hours under a nitrogen atmosphere. To this was added dropwise 2,3-dihydro-1,4-benzodioxin-2methanamine hydrochloride (1.2 g, 6.0 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions were concentrated and washed with a minimum amount of THF to remove a by-product and to give 1.2 g (57%) of the desired product, (2,3-dihydro-benzo [1,4] dioxin-2-ylmethyl)-4-(1H-indol-3-yl)-butanamide, as an oil.

Lithium aluminum hydride (1.3 g, 34 mmole) in dry THF (100 ml) was placed in a three-neck flask which was flushed with nitrogen. The amide (1.2 g, 3.4 mmole) prepared above in 50 ml of dry THF was slowly introduced through a syringe to the LAH suspension in an ice-bath. The mixture was then stirred at gentle reflux for 24 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using ethyl acetate to give 0.8 g (71%, 2.4 mmole) of the free base of the expected product as a white solid. The free base was dissolved in 50 ml of ethanoldiethyl ether (1:1) and treated with 0.25M fumaric acid in ethanol (5.3 ml, 1.32 mmole) to give the title compound as a white solid, (2:1) fumarate salt, quarter hydrate, m.p. 200°–201° C.

Elemental Analysis for: $C_{21}H_{24}N_2O_2 \cdot \frac{1}{2}C_4H_4O_4 \cdot \frac{1}{4}H_2O$ Calc'd: C, 69.24; H, 6.70; N, 7.02 Found: C, 69.55; H, 6.53; N, 6.89

EXAMPLE 17

(2,3-Dihydro-benzo[1,4]dioxin-2-ylmethyl)-[3-(1H-indol-3-yl)-propyl]-amine

3-Indolepropionic acid (1.1 g, 6.0 mmole), 1-hydroxybenzotriazole hydrate (0.97 g, 7.2 mmole) and 1,3-diisopropylcarbodiimide (2.3 ml, 14.4 mmole) were combined in 100 ml of DMF and stirred at room temperature for 2 hours under a nitrogen atmosphere. To this was added dropwise 2,3-dihydro-1,4-benzodioxin-2-methanamine hydrochloride (1.2 g, 6.0 mmole) in 50 ml of DMF, and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions containing product were concentrated and washed with a minimum amount of THF to remove a by-product and to give 1.2 g (60%) of the desired product, (2,3-dihydrobenzo [1,4]dioxin-2-ylmethyl)-4-(1H-indol-3-yl)-propanamide, as an oily solid.

Lithium aluminum hydride (1.4 g, 36mmole) in dry THF (100 ml) was placed in a three-necked flask which was flushed with nitrogen. The amide (1.2 g, 3.6 mmole) prepared above in 50 ml of dry THF was slowly introduced through a syringe to the LAH suspension in an ice-bath. The mixture was then stirred at gentle reflux for 24 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using first ethyl acetate and then 2.5% methanol in ethyl acetate to give 0.8 g (69%, 2.5 mmole) of the free base of the expected product as an off-white solid. The free base was dissolved in ethanoldiethyl ether (1:1) and treated with 0.25M fumaric acid in ethanol (5.5 ml, 1.38 mmole) to give the title compound as a white solid, (2:1) fumarate salt, quarter hydrate, m.p. 174°–175° C.

Elemental Analysis for: $C_{20}H_{22}N_2O_2 \cdot \frac{1}{2}C_4H_4O_4 \cdot \frac{1}{4}H_2O$ Calc'd: C, 68.64; H, 6.42; N, 7.28 Found: C, 69.00; H, 6.19; N, 7.17

EXAMPLE 18

(2,3-Dihydro-benzo[1,4]dioxin-2-ylmethyl)-[4-(5-fluoro-1H-indol-3-yl)-butyl]-amine 5-Fluoroindole-3-butyric acid (1.5 g, 6.8 mmole), 1-hydroxybenzotriazole hydrate (1.1 g, 8.2 mmole) and 1,3-diisopropylcarbodiimide (2.6 ml, 16.3 mmole) were combined in 150 ml of DMF and stirred at room temperature for 2 hours under a nitrogen atmosphere. To this was added dropwise 2,3-dihydro-1,4-benzodioxin-2-methanamine hydrochloride (1.4 g, 6.8 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions of the products were concentrated and washed with a minimum amount of THF to remove a by-product and to give 1.5 g (60%) of the desired product, (2,3-dihydrobenzo[1,4]dioxin-2-ylmethyl)-4-(5-fluoro-1H-indole-3yl)-butanamide, as an oil.

Lithium aluminum hydride (1.5 g, 41 mmole) in dry THF (100 ml) was placed in a three-neck flask which was flushed with nitrogen. The amide (1.5 g, 4.1 mmole) prepared above in 50 ml of dry THF was slowly introduced through a syringe to the LAH suspension in an ice-bath. The mixture was then stirred at gentle reflux for 24 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using ethyl acetate to give 1.1 g (76%, 3.1 mmole) of the free base of the expected product as an oil. The free base was dissolved in 30 ml of ethanol-diethyl ether (1:1) and treated with 0.25M fumaric acid in ethanol (6.8 ml, 1.7 mmole). To this was added several drops of hexane to precipitate the title compound as a snowy white solid, (2:1) fumarate, m.p. 195° C.

Elemental Analysis for: $C_{21}H_{23}FN_2O_2 \cdot \frac{1}{2}C_4H_4O_4$ Calc'd: C, 66.98; H, 6.11; N, 6.79 Found: C, 66.80; H, 6.17; N, 6.59

EXAMPLE 19

[4-(5-Fluoro-1H-indole-3-yl)-butyl]-(7-methoxy-2,3-dihydro-benzo[1,4]dioxin-2-ylmethyl)-amine 5-Fluoroindole-3-butyric acid (1.2 g, 5.4 mmole), 1-hydroxybenzotriazole hydrate (0.88 g, 6.5 mmole) and 1,3-diisopropylcarbodiimide (2.0 ml, 13.0 mmole) were combined in 150 ml of DMF and stirred at room temperature for 2 hours under a nitrogen atmosphere. To this was added dropwise 7-methoxy-2,3-dihydro-1,4-benzodioxin-2-methanamine hydrochloride (1.3 g, 5.4 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions containing product were concentrated and washed with a minimum amount of THF to remove a by-product and to give 1.2 g (56%) of the desired product, (7-methoxy-2, 3-dihydro-benzo[1,4]dioxin-2-ylmethyl)-4-(5-fluoro-1H-indole-3-yl)-butanamide, as an oil.

Lithium aluminum hydride (1.1 g, 30 mmole) in dry THF (100 ml) was placed in a three-neck flask which was flushed with nitrogen. The amide (1.2 g, 3.0 mmole) prepared above in 50 ml of dry THF was slowly introduced through a syringe to the LAH suspension in an ice-bath. The mixture was then stirred at gentle reflux for 24 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using ethyl acetate to give 0.75 g (65%, 2.0 mmole) of the free base of the expected product as a colorless oil. The free base was dissolved in 50 ml of ethanol-diethyl ether (1:1) and treated with 0.25M fumaric acid in ethanol (4.3 ml, 01.08 mmole). To this was added several drops of n-hexane to precipitate the title compound as a snowy white solid, (2:1) fumarate salt, m.p. 185° C.

Elemental Analysis for: $C_{22}H_{25}FN_2O_3 \cdot \frac{1}{2}C_4H_4O_4$ Calc'd: C, 65.15; H, 6.15; N, 6.33 Found: C, 64.91; H, 6.08; N, 6.02

EXAMPLE 20

3-{[3-(1H-Indol-3-yl)-propylamino]methyl}-2,3-dihydro-benzo[1,4]dioxin-6-ol

3-Indolepropionic acid (1.4 g, 7.4 mmole), 1-hydroxybenzotriazole hydrate (1.2 g, 8.9 mmole) and 1,3-diisopropylcarbodiimide (2.8 ml, 17.8 mmole) were combined in 100 ml of DMF and stirred at room temperature for 2 hours under a nitrogen atmosphere. To this was added dropwise (S)-7-hydroxy-2,3-dihydro-1,4-benzodioxin-2-methanamine hydrochloride (1.6 g, 7.4 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions containing product were concentrated and washed with a minimum amount of THF to remove a by-product and to give 1.5 g (60%) of the desired product, (S)-(7-hydroxy-2,3-dihydro-benzo[1,4]dioxin-2-ylmethyl)-4-(1H-indol-3-yl)-propanamide, as a white fluffy solid.

Lithium aluminum hydride (1.7 g, 45 mmole) in dry THF (100 ml) was placed in a three-neck flask which was flushed with nitrogen. The amide (1.5 g, 4.5 mmole) prepared above in 50 ml of dry THF was slowly introduced through a syringe to the LAH suspension in an ice-bath. The mixture was then stirred at gentle reflux for 48 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using ethyl acetate to give 0.6 g (39%, 1.8 mmole) of the free base of the expected product as a white solid. The free base was dissolved in 20 ml of ethanol and treated with 0.25M fumaric acid in ethanol (3.9 ml, 0.98 mmole). To this was added several drops of n-hexane to precipitate the (S) enantiomer of the title compound as a yellowish, white solid, (2:1) fumarate salt, quarter hydrate, m.p. 189°–190° C.

Elemental Analysis for: $C_{20}H_{22}N_2O_3 \cdot \frac{1}{2}C_4H_4O_4 \cdot \frac{1}{4}H_2O$ Calc'd: C, 65.90; H, 6.16; N, 6.99 Found: C, 66.03; H, 6.01; N, 7.02

EXAMPLE 21

N-(3-{[3-(1H-Indol-3-yl)-propylamino]methyl}-2,3-dihydro-benzo[1,4]dioxin-6-yl)-methanesulfonamide 3-Indolepropionic acid (0.77 g, 4.1 mmole), 1-hydroxybenzotriazole hydrate (0.66 g, 4.9 mmole) and 1,3-diisopropylcarbodiimide (0.77 ml, 4.9 mmole) were combined in 75 ml of DMF and stirred at room temperature for 2 hours under a nitrogen atmosphere. To this was added dropwise 7-methylsulfonylamino-2,3-dihydro-1,4-benzodioxin-2-methanamine (1.0 g, 4.1 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using 10% hexane in ethyl acetate as the eluant. Fractions containing product were concentrated and washed with a minimum amount of THF to remove a by-product and to give 1.1 g (61%) of the desired product, (S)-(7-methylsulfonyl-2,3-dihydro-benzo[1,4]dioxin-2-ylmethyl)-4-(1H-indol-3-yl)-propanamide, as a white solid.

Lithium aluminum hydride (0.9 g, 25 mmole) in dry THF (100 ml) was placed in a three-neck flask which was flushed with nitrogen. The amide (1.1 g, 2.5 mmole) prepared above in 50 ml of dry THF was slowly introduced through a syringe to the LAH suspension in an ice-bath. The mixture was then stirred at gentle reflux for 48 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using ethyl acetate to give 0.5 g (50%, 1.3 mmole) of the free base of the expected product as a white solid. The free base was dissolved in ethanol (20 ml) and treated with 0.25M fumaric acid in ethanol (2.7 ml, 0.68 mmole). To this was added several drops of hexane to give the (S) enantiomer of the title compound as a light tan solid, (2:1) fumarate, quarter hydrate, m.p. 141°–142° C.

Elemental Analysis for: $C_{21}H_{25}N_3O_4S \cdot \frac{1}{2}C_4H_4O_4 \cdot \frac{1}{4}H_2O$ Calc'd: C, 57.79; H, 5.80; N, 8.79 Found: C, 57.60; H, 5.80; N, 8.52

EXAMPLE 22

(2,3-Dihydro-benzo[1,4]dioxin-2-ylmethyl)-{4-[5-fluoro-1-methyl-1H-(indole-3-yl)]-butyl}-amine 5-Fluoro-1-methylindole-3-butyric acid (1.4 g, 6.0 mmole), 1-hydroxybenzotriazole hydrate (1.0 g, 7.2 mmole) and 1,3-diisopropylcarbodiimide (2.3 ml, 14.4 mmole) were combined in 150 ml of DMF and stirred at room temperature for 2 hours under a nitrogen atmosphere. To this was added dropwise 2,3-dihydro-1,4-benzodioxin-2-methanamine hydrochloride (1.2 g, 6.0 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions containing product were concentrated and washed with a minimum amount of THF to remove a by-product and to give 1.0 g (44%) of the desired product, (2,3-dihydro-benzo[1,4]dioxin-2-ylmethyl)-4-(5-fluoro-1-methyl-1H-indole-3-yl)butanamide, as a pale yellow solid.

Lithium aluminum hydride (1.0 g, 26 mmole) in dry THF (75 ml) was placed in a three-neck flask which was flushed with nitrogen. The amide (1.0 g, 2.6 mmole) prepared above in 30 ml of dry THF was slowly introduced through a syringe to the LAH suspension in an ice-bath. The mixture was then stirred at gentle reflux for 4 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on silica gel using ethyl acetate to give 0.8 g (84%, 2.3 mmole) of the free base of the expected product as a colorless oil. The free base was dissolved in 40 ml of ethanol-diethyl ether (1:1) and treated with 0.25M fumaric acid in ethanol (5.0 ml, 1.25 mmole) to give the title compound as a white solid, (2:1) fumarate salt, m.p. 160° C.

Elemental Analysis for: $C_{22}H_{25}FN_2O_2 \cdot \frac{1}{2}C_4H_4O_4$ Calc'd: C, 67.59; H, 6.38; N, 6.57 Found: C, 67.53; H, 6.40; N, 6.56

EXAMPLE 23

(2,3-Dihydro-benzo[1,4]dioxin-2-ylmethyl)-[4-(5-methoxy-1H-indol-3-yl)-butyl]-amine 5-methoxyindole-3-butyric acid (1.5 g, 6.4 mmole), 1-hydroxybenzotriazole hydrate (1.0 g, 7.7 mmole) and 1,3-diisopropylcarbodiimide (2.4 ml, 15.4 mmole) were combined in 150 ml of DMF and stirred at room temperature for 2 hours under a nitrogen atmosphere. To this was added dropwise 2,3-dihydro-1,4-benzodioxin-2-methanamine hydrochloride (1.3 g, 6.4 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions containing product were concentrated and washed with a minimum amount of TBF to remove a by-product and to give 1.8 g (74%) of the desired product, (2,3-dihydrobenzo[1,4]dioxin-2-ylmethyl)-4-(5-1H-indole-3-yl)-butanamide, as an oil.

Lithium aluminum hydride (1.8 g, 47 mmole) in dry THF (100 ml) was placed in a three-neck flask which was flushed with nitrogen. The amide (1.8 g, 4.7 mmole) prepared above in 50 ml of dry THF was slowly introduced through a syringe to the LAH suspension in an ice-bath. The mixture was then stirred at gentle reflux for 24 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude free base (1.6 g, 4.4 mmole) was dissolved in 25 ml of ethanol-diethyl ether (1:1) and treated with 0.25M fumaric acid in ethanol (9.7 ml, 2.4 mmole) to give a solid, which was recrystallized from ethanol to afford the title compound as an ivory solid, (2:1) fumarate salt, quarter hydrate, m.p. 182°–183° C.

Elemental Analysis for: $C_{22}H_{26}N_2O_3 \cdot \frac{1}{2}C_4H_4O_4 \cdot \frac{1}{4}H_2O$
Calc'd: C, 67.19; H, 6.70; N, 6.53 Found: C, 67.21; H, 6.83; N, 6.43

EXAMPLE 24

N-(3-{[3-(1-Methyl-1H-indol-3-yl)-propylamino]-methyl}-2,3-dihydrobenzo[1,4]dioxin-6-yl)-methanesulfonamide 1-Methylindole-3-propionic acid (1.2 g, 6.0 mmole), 1-hydroxybenzotriazole hydrate (0.97 g, 7.2 mmole) and 1,3-diisopropylcarbodiimide (1.1 ml, 7.2 mmole) were combined in 100 ml of DMF and stirred at room temperature for 2 hours under a nitrogen atmosphere. To this was added dropwise 7-methylsulfonylamino-2,3-dihydro-1,4-benzodioxin-2-methanamine (1.9 g, 7.2 mmole) in 50 ml of DMF and the mixture was further stirred for 24 hours. The solvent was removed and the residue partitioned between dichloromethane and water. The separated dichloromethane layer was dried over anhydrous sodium sulfate, filtered and concentrated in vacuum. The residue was chromatographed on a silica gel column using ethyl acetate as the eluant. Fractions containing product were concentrated and washed with a minimum amount of THF to remove a by-product and to give 2.1 g (79%) of the desired product, (7-methylsulfonyl-2,3-dihydro-benzo[1,4]dioxin-2ylmethyl)-4-(1-methyl-1H-indol-3-yl)-propanamide, as a fluffy white solid.

Lithium aluminum hydride (1.8 g, 47 mmole) in dry THF (150 ml) was placed in a three-neck flask which was flushed with nitrogen. The amide (2.1 g, 4.7 mmole) prepared above in 75 ml of dry THF was slowly introduced through a syringe to the LAH suspension in an ice-bath. The mixture was then stirred at gentle reflux for 24 hours. After the reaction mixture cooled to room temperature, the hydride was carefully destroyed with 5 ml of 1:1 mixture of THF and water in an ice-bath. Stirring was continued as 15 ml of 2.5N NaOH solution was added to coagulate the precipitate of aluminum hydroxide. The precipitate was filtered and washed with dichloromethane/isopropanol (3/1) solution. The filtrate was dried over anhydrous sodium sulfate, filtered and concentrated. The crude product was chromatographed on a silica gel using ethyl acetate to give 0.6 g (30%, 1.4 mmole) of the free base of expected product as a white solid. The free base was dissolved in ethanol (15 ml) and treated with 0.25M fumaric acid in ethanol (3.0 ml, 0.75 mmole). To this was added several drops of hexane to give the title compound as a light yellow solid, (2:1) fumarate salt, hemihydrate, m.p. 125°–128° C.

Elemental Analysis for: $C_{22}H_{27}N_3O_4S \cdot \frac{1}{2}C_4H_4O_4 \cdot \frac{1}{2}H_2O$
Calc'd: C, 58.05; H, 6.09; N, 8.46 Found: C, 58.08; H, 5.99; N, 8.17

What is claimed is:
1. A compound of formula I:

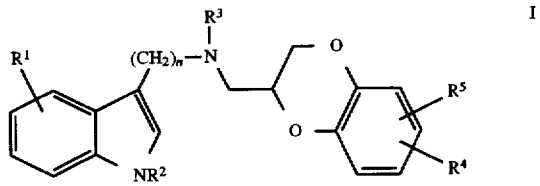

wherein
$R^1$, $R^4$ and $R^5$ are, independently, hydrogen, alkyl of 1–6 carbon atoms, alkoxy of 1–6 carbon atoms, aralkoxy of 7 to 12 carbon atoms, alkanoyloxy of 2 to 6 carbon atoms, hydroxy, halo, trifluoromethyl, amino, mono- or di-alkylamino in which each alkyl group has 1 to 6 carbon atoms, alkanamido of 2 to 6 carbon atoms, or alkanesulfonamido of 1 to 6 carbon atoms; or, $R^1$ is defined as above and $R^4$ and $R^5$, taken together, are ortho substituted methylenedioxy, ethylenedioxy, or propylenedioxy;

$R^2$ and $R^3$ are, independently, hydrogen or alkyl of 1 to 6 carbon atoms;

n is 3 or 4;

or a pharmaceutically acceptable salt thereof.

2. A compound of claim 1 in which $R^1$, $R^4$ and $R^5$ are hydrogen, hydroxy, alkoxy of 1 to 6 carbon atoms, halo or alkanesulfonamido of 1 to 6 carbon atoms; or, $R^1$ is hydrogen, hydroxy, alkoxy of 1 to 6 carbon atoms, halo or alkanesulfonamido of 1 to 6 carbon atoms, and $R^4$ and $R^5$, taken together, are methylenedioxy; and $R^2$ and $R^3$ are hydrogen; or a pharmaceutically acceptable salt thereof.

3. A compound of claim 1 in which $R^1$ is hydrogen, hydroxy, methoxy or fluoro; $R^2$, $R^3$ and $R^5$ are hydrogen; $R^4$ is hydrogen, hydroxy, methoxy, ethoxy, halo or alkanesulfonamido of 1 to 3 carbon atoms; or a pharmaceutically acceptable salt thereof.

4. The compound of claim 1 which is [(6,7-dihydro-1,3-dioxolo[4,5-g][1,4]benzodioxin-6-yl)methyl]-[4-(1H-indol-3-yl)-butyl]-amine or a pharmaceutically acceptable salt thereof.

5. The compound of claim 1 which is [4-(1H-indol-3-yl)-butyl]-(7-methoxy-2,3-dihydro-benzo[1,4]dioxin-2-ylmethyl)-amine or a pharmaceutically acceptable salt thereof.

6. The compound of claim 1 which is 3-{[4-(1H-indol-3-yl)-butylamino]-methyl}-2,3-dihydro-benzo[1,4]dioxin-6-ol or a pharmaceutically acceptable salt thereof.

7. The compound of claim 1 which is [3-(5-benzyloxy-1H-indol-3-yl)-propyl]-(2,3-dihydro-benzo[1,4]dioxin-2-ylmethyl)-amine or a pharmaceutically acceptable salt thereof.

8. The compound of claim 1 which is 3-{3-[(2,3-dihydro-benzo[1,4]dioxin-2-ylmethyl)-amino]-propyl}-1H-indol-5-ol or a pharmaceutically acceptable salt thereof.

9. The compound of claim 1 which is 3-{3-[(7-methoxy-2,3-dihydrobenzo[1,4]dioxin-2-ylmethyl)-amino]-propyl}-1H-5-ol )-1H-indol-5-ol or a pharmaceutically acceptable salt thereof.

10. The compound of claim 1 which is (7-methoxy-2,3-dihydrobenzo-[1,4]dioxin-2-ylmethyl)-[3-(5-methoxy-1H-indol-3-yl)-propyl]-methyl-amine or a pharmaceutically acceptable salt thereof.

11. The compound of claim 1 which is 3-{3-[(7-hydroxy-2,3-dihydrobenzo-[1,4]dioxin-2-ylmethyl)-amino]-propyl}-1H-indol-5ol or a pharmaceutically acceptable salt thereof.

12. The compound of claim 1 which is (7-methoxy-2,3-dihydrobenzo-[1,4]dioxin-2-ylmethyl)-[4-(5-methoxy-1H-indol-3-yl)-butyl]-amine or a pharmaceutically acceptable salt thereof.

13. The compound of claim 1 which is 3-{[4-(5-methoxy-1H-indol-3-yl)-butylamino]-methyl}-2,3-dihydro-benzo[1,4]dioxin-6-ol or a pharmaceutically acceptable salt thereof.

14. The compound of claim 1 which is N-(3-{[4-(1H-indol-3-yl)-butylamino]-methyl}-2,3-dihydro-benzo[1,4]dioxin-6-yl)-methanesulfonamide or a pharmaceutically acceptable salt thereof.

15. The compound of claim 1 which is (2,3-dihydro-benzo[1,4]dioxin-2-ylmethyl)-[3-(5-methoxy-1H-indol-3-yl)-propyl]-amine or a pharmaceutically acceptable salt thereof.

16. The compound of claim 1 which is (2,3-dihydro-benzo[1,4]dioxin-2-ylmethyl)-[3-(5-fluoro-1H-indol-3yl)-propyl]-amine or a pharmaceutically acceptable salt thereof.

17. The compound of claim 1 which is N-(3-{[4-(5-methoxy-1H-indol-3-yl)-butylamino]-methyl}-2,3-dihydro-benzo[1,4]dioxin-6-yl)methanesulfonamide or a pharmaceutically acceptable salt thereof.

18. The compound of claim 1 which is [3-{[4-(1H-ndol-3-yl)-propylamino]-methyl}-2,3-dihydro-benzo[1,4]dioxin-6-ol] 3-{[4-(1H-indol-3-yl)propylamino]-methyl}-2,3-dihydro-benzo[1,4]dioxin-6-ol or a pharmaceutically acceptable salt thereof.

19. The compound of claim 1 which is (2,3-dihydro-benzo[1,4]dioxin-2-ylmethyl)-[4-(1H-indol-3-yl)-butyl]-amine or a pharmaceutically acceptable salt thereof.

20. The compound of claim 1 which is (2,3-dihydro-benzo[1,4]dioxin-2-ylmethyl)-[3-(1H-indol-3-yl)-propyl]-amine or a pharmaceutically acceptable salt thereof.

21. The compound of claim 1 which is (2,3-dihydro-benzo[1,4]dioxin-2-ylmethyl)-[4-(5-fluoro-1H-indol-3-yl)-butyl]-amine or a pharmaceutically acceptable salt thereof.

22. The compound of claim 1 which is [4-(5-fluoro-1H-indole-3-yl)-butyl]-(7-methoxy-2,3-dihydro-benzo[1,4]dioxin-2-ylmethyl)-amine or a pharmaceutically acceptable salt thereof.

23. The compound of claim 1 which is 3-{[3-(1H-indol-3-yl)-propylamino]-methyl}-2,3-dihydro-benzo[1,4]dioxin-6-ol or a pharmaceutically acceptable salt thereof.

24. The compound of claim 1 which is N-(3-{[3-(1H-indol-3-yl)-propylamino]-methyl}-2,3-dihydro-benzo[1,4]dioxin-6-yl)-methanesulfonamide or a pharmaceutically acceptable salt thereof.

25. The compound of claim 1 which is (2,3-dihydro-benzo[1,4]dioxin-2-ylmethyl)-{4-[5-fluoro-1-methyl-1H-(indole-3-yl)]-butyl}-amine or a pharmaceutically acceptable salt thereof.

26. The compound of claim 1 which is (2,3-dihydro-benzo[1,4]dioxin-2-ylmethyl)-[4-(5-methoxy-1H-indol-3-yl)-butyl]-amine or a pharmaceutically acceptable salt thereof.

27. The compound of claim 1 which is N-(3-{[3-(1-methyl-1H-indol-3-yl)-propylamino]-methyl}-2,3-dihydro-benzo[1,4]dioxin-6-yl)methanesulfonamide or a pharmaceutically acceptable salt thereof.

* * * * *